United States Patent

Reuss, Jr. et al.

[19]

[11] Patent Number: 5,928,935
[45] Date of Patent: Jul. 27, 1999

[54] BIOLOGICAL SPECIMEN CONTAINMENT AND INCUBATION DEVICE

[76] Inventors: William Alexander Reuss, Jr., 4901 Lea Ann Way, Louisville, Ky. 40219; William Charles Mers Kelly, 1112 Glen Kegley Dr., Xenia, Ohio 45385; David Young Piteups, 904 Shady La., Anchorage, Ky. 40223

[21] Appl. No.: 08/877,524

[22] Filed: Jun. 17, 1997

Related U.S. Application Data

[63] Continuation-in-part of application No. 08/534,051, Sep. 26, 1995, Pat. No. 5,681,742.

[51] Int. Cl.$^6$ ...................................................... C12M 1/24
[52] U.S. Cl. ..................................... 435/288.1; 435/304.1; 435/307.1; 422/102; 356/246; 215/307; 215/313; 220/350; 220/367.1; 604/403
[58] Field of Search ............................ 435/288.1, 288.2, 435/304.1, 304.2, 307.1; 422/102; 356/246; 359/398; 215/277, 307, 311, 313, 355; 220/203.06, 203.09, 203.11, 203.13, 203.14, 303, 787, 351, 360, 367.1, 602, 662, 663, 350; 604/403, 415; D9/439, 440; D24/224

[56] References Cited

U.S. PATENT DOCUMENTS

| | | |
|---|---|---|
| Re. 35,167 | 3/1996 | Mouchawar et al. . |
| D. 222,352 | 10/1971 | Ferro et al. . |
| D. 380,555 | 7/1997 | Kuorsaki et al. . |
| 1,180,665 | 4/1916 | McElroy . |
| 2,142,278 | 1/1939 | Mendelson . |
| 2,797,837 | 7/1957 | Roberts . |
| 2,881,937 | 4/1959 | Roberts . |
| 3,814,522 | 6/1974 | Clark et al. . |
| 4,650,662 | 3/1987 | Goldfinger et al. . |
| 4,902,286 | 2/1990 | Ranoux . |
| 5,135,865 | 8/1992 | Ranoux . |
| 5,297,599 | 3/1994 | Bucheli . |
| 5,342,347 | 8/1994 | Kikuchi et al. . |
| 5,620,434 | 4/1997 | Brony . |
| 5,681,742 | 10/1997 | Merskelly et al. . |

*Primary Examiner*—William H. Beisner
*Attorney, Agent, or Firm*—Don Halgren

[57] ABSTRACT

The present invention comprises a biological specimen container assembly for the safe storage and periodic examination of biological specimens therein, which includes an elongated vial having a primary chamber with a first open end and a second closed end. The second closed end on the vial has a secondary chamber therein of generally rectilinear shape in cross-section. A valve having a first end and a second end, has its second end matable with the first open end of the vial, the valve having an adjustably openable and closable bore extending longitudinally therethrough. A hard cap has a cavity therein which is matable over the first end of the valve. An end cap is matable over the hard cap and the valve, the end cap being arranged to maintain sterility of the end cap, the valve and the first end of the vial.

18 Claims, 8 Drawing Sheets

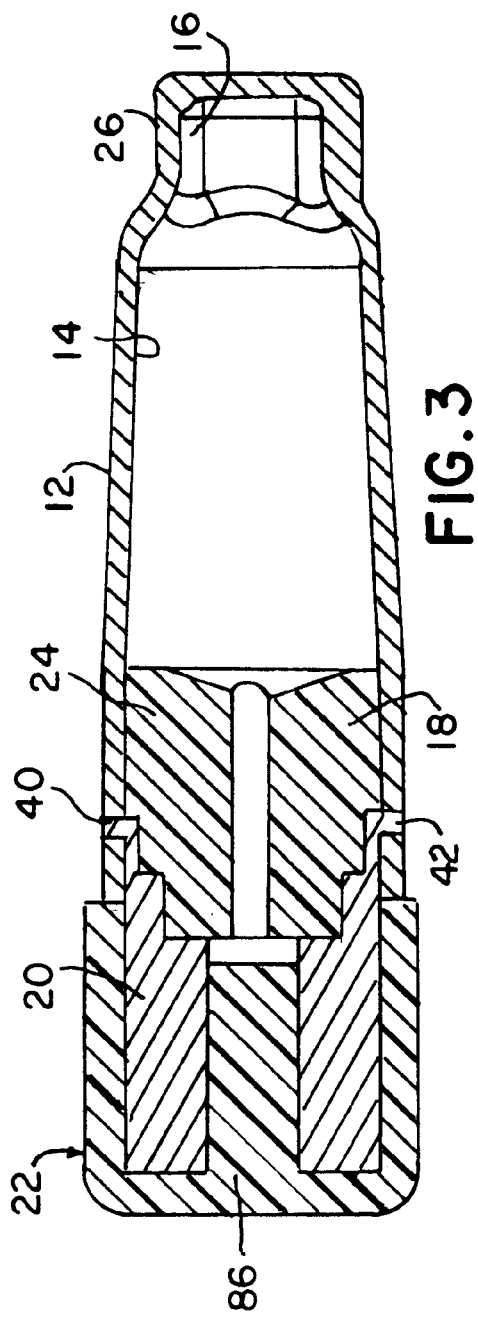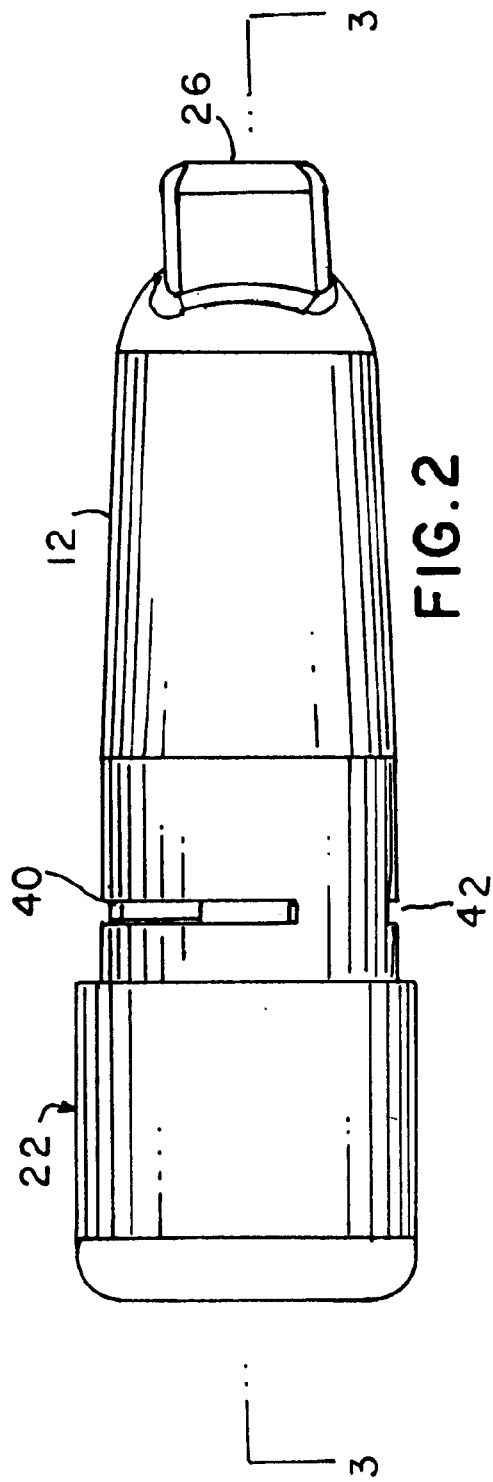

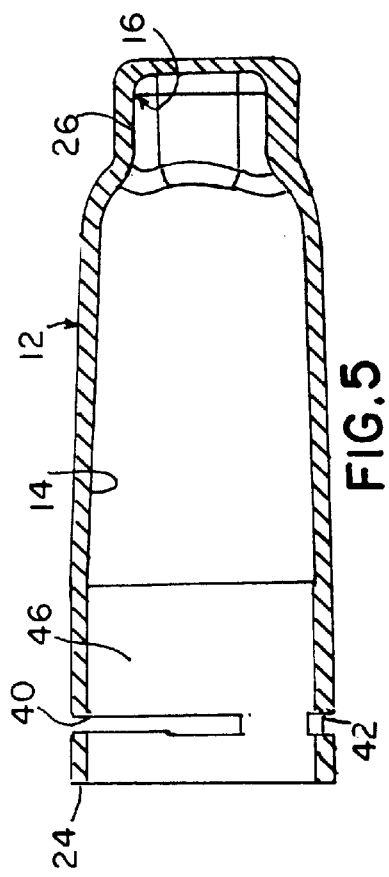
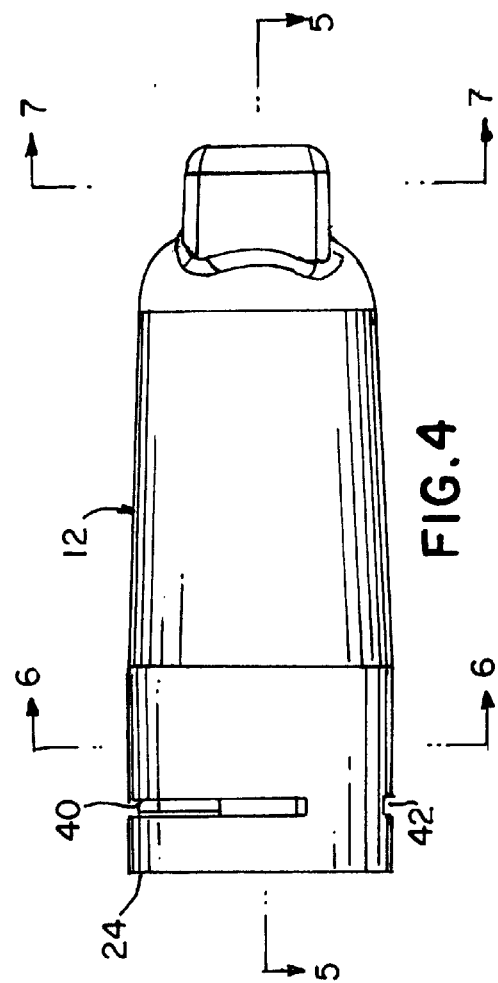
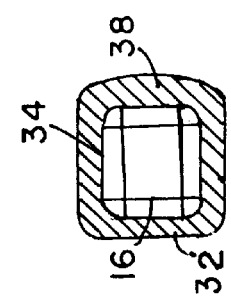
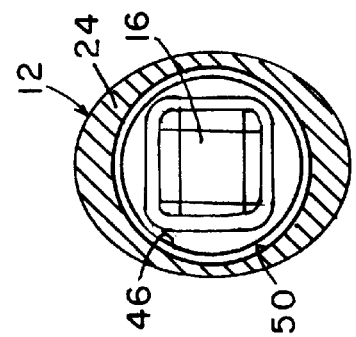

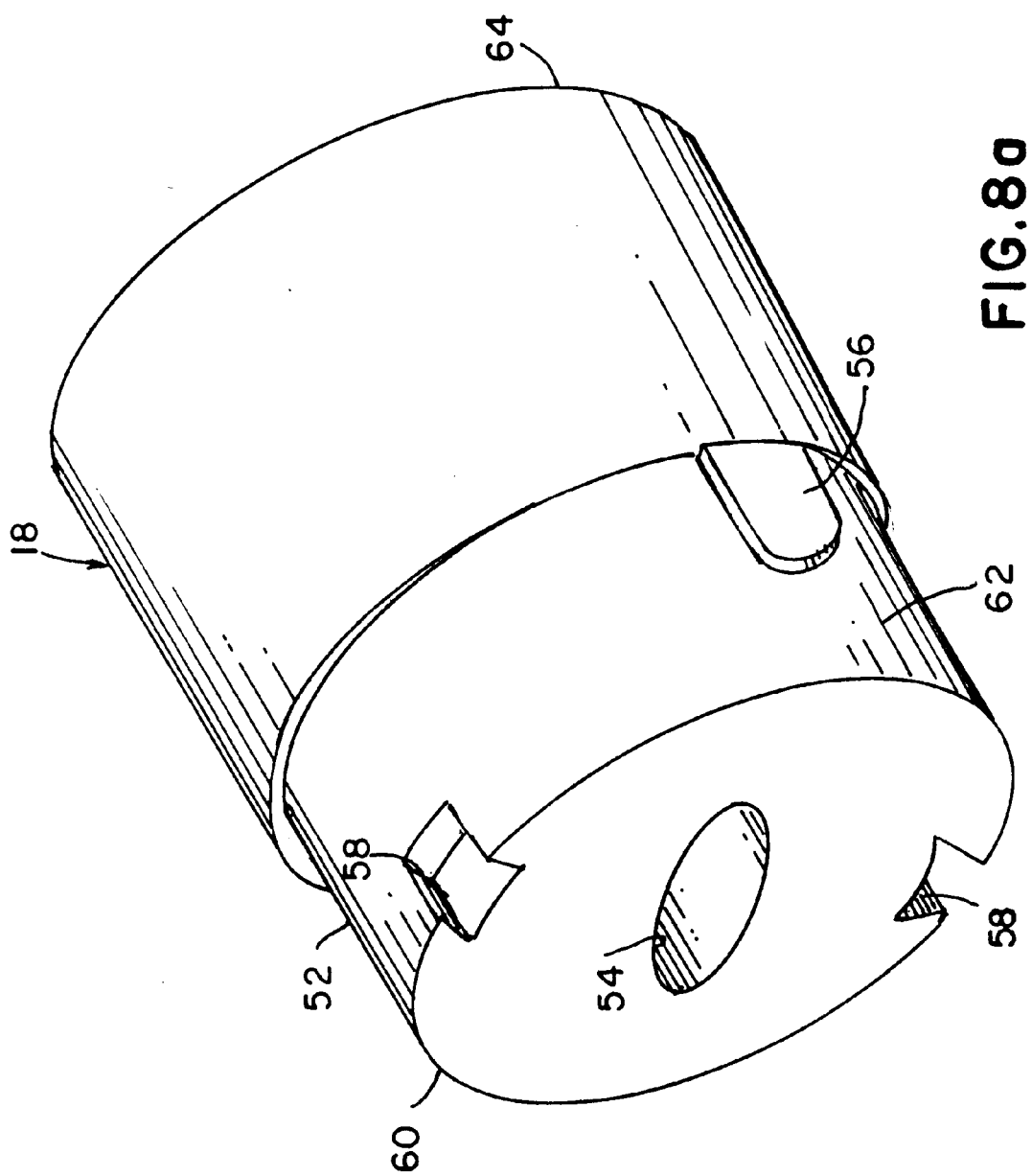

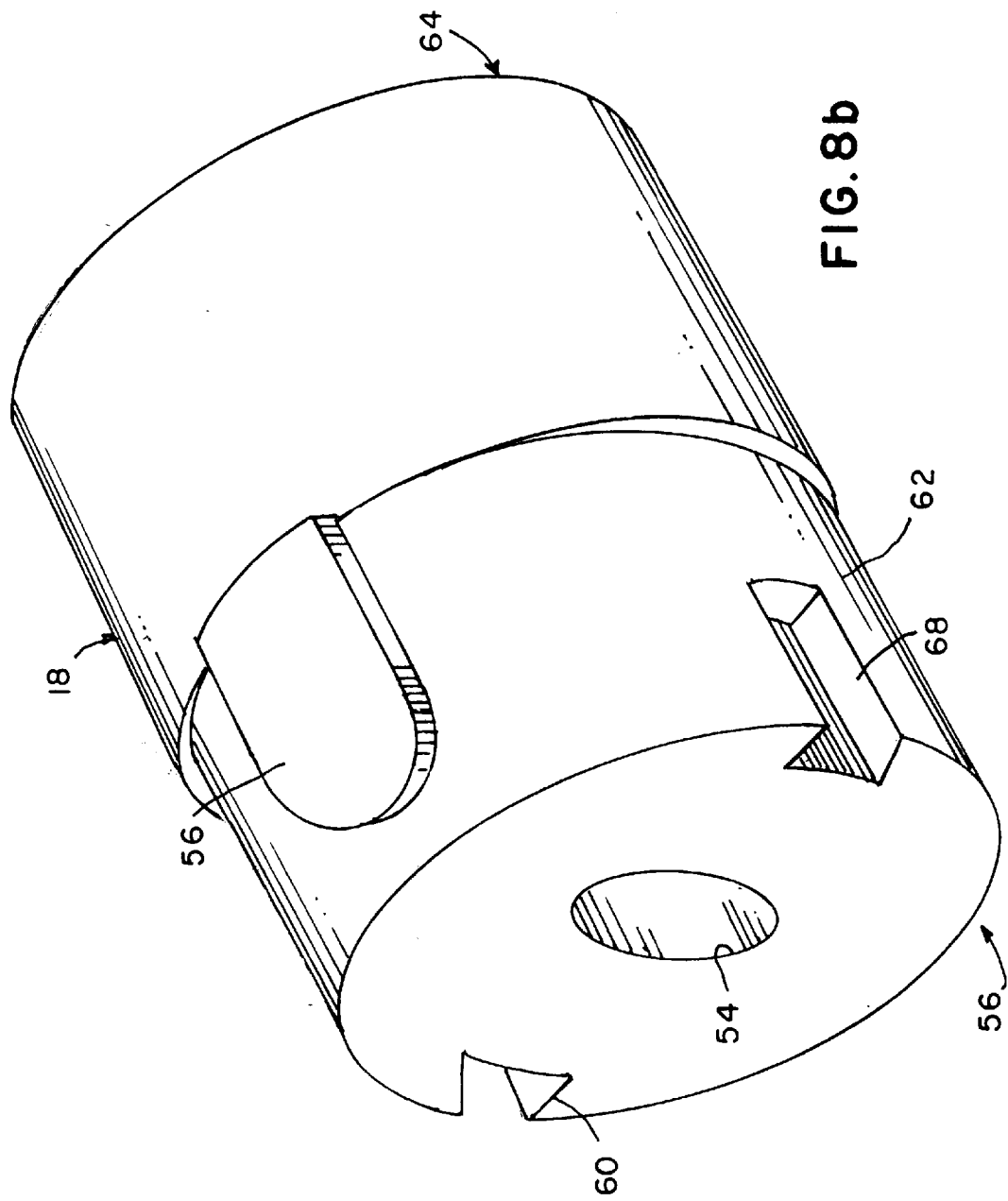

BIOLOGICAL SPECIMEN CONTAINMENT AND INCUBATION DEVICE

This application is a continuation-in-part application of our earlier filed, U.S. patent application Ser. No. 08/534,051, filed Sep. 26, 1995, now U.S. Pat. No. 5,681,742 which is incorporated herein by reference, in its entirety.

BACKGROUND OF THE INVENTION

1. Field of the Invention

This invention relates to biological specimen containment devices, and more particularly to a chamber useful for in vitro fertilization cultures.

2. Prior Art

Containment devices for biological specimens often are restricted in their design function. The devices often must not permit light to strike the medium within the container. The device must not have sharp edges which would bind or unintentionally agitate the medium within the container. The device must also often permit the medium to be maintained at a desired precise temperature, and the device must often minimize the exposure of the medium to the atmosphere.

One such containment device is shown in U.S. Pat. No. 4,598,045 to Masover et al. issued on Jul. 1, 1986. This patent discloses a container shaped like a cylinder, having a screw on cap. The container however, is designed to permit microscopic examination of the medium without opening of the container.

A further biological specimen containment device is shown in U.S. Pat. No. 4,761,379 to Williams et al. this device however, utilizes a wide-natured opening, which could expose many biological specimens to the atmosphere for too long a period of time, and as such, would not be useful for procedures involving specimens for example, in vitro fertilization processes because of potential atmospheric contamination.

A further biological container is described in U.S. Pat. No. 5,135,865 to Ranoux, wherein a thin walled tube having a rounded lower end and a screw-on cap on its upper end, for containment and fertilization of human ovocytes with minimal $CO_2$ exposure to the medium.

It is an object of the present invention to provide a biological specimen container which overcomes the disadvantages of the prior art.

It is a further object of the present invention to provide a biological container which readily permits visual examination of the contents of the container, from the outside thereof.

It is yet a further object of the present invention, to provide a biological specimen container which permits samples to be taken thereof, without the likelihood of damaging the specimen within the container.

BRIEF SUMMARY OF THE INVENTION

The present invention comprises of a biological specimen container arranged to safely support a biological specimen in a controlled environment, such as in the uterus of a female.

The container comprises a vial body portion comprising a primary chamber and a second chamber of reduced internal and external dimensions, a rubber stopper, a hard cap, and a rubber diaphragm cover. The vial body portion is general y cylindrically shaped, having an opened first end and a viewable closed second end. The closed second end that comprises the second chamber, is of a generally rectangular configuration in a transverse cross sectional orientation. That is, the walls defining the viewable portion are of rectangular configuration, having a two pairs of opposed walls, one of the pair of walls being thicker and of lens shape in cross section, so as to act as a focal area for visual viewing of a specimen contained within that viewable volume at the closed end of the vial body. One of the pairs of side walls of the viewable portion of the vial body closed end, has a thinner wall section, to permit microscopic examination of the contents of that volume within that closed viewable end of the vial body.

The vial body has a main chamber of generally cylindrical configuration. The first end of the vial body has a pair of opposed slots, which are cut through the side wall of the vial body adjacent the first opened end thereof. Each slot extends approximately through an arc of about one hundred and twenty degrees. The chamber has a wall portion inwardly of the slots, which walls define an elliptical opening adjacent the generally cylindrically shaped container chamber. The vial body may be made of a clear polycarbonate.

The vial body has a rubber stopper or valve which is cylindrically shaped on its open or first end. The rubber stopper or valve has a longitudinal axis which corresponds to the longitudinal axis of the vial body. The rubber stopper has an elliptically shaped bore extending longitudinally therethrough. The rubber stopper has a first end comprising approximately one-half the longitudinally length of the rubber stopper with a pair of opposed axially extending side taps thereon adjacent the annular surface thereof. Spaced ninety degrees apart from the side tabs, are a pair of channel shaped cut-outs. The periphery of the outer surface of the first end of the rubber stopper, defines a circular configuration, but for the side tabs. The second end of the rubber stopper, contiguous to the first end, comprising the second longitudinal half thereof, is of elliptical configuration. The second end of the rubber stopper has a conically shaped opening which is in longitudinal alignment with the elliptical disposed bore extending through the rubber stopper.

The vial assembly includes a hard cap. The hard cap is a cup-shaped shell having a first end and a second end. The first end has a hole extending therethrough, at a centermost location. The side walls of the first end have a pair of opposed accurate shaped cut-outs disposed thereacross. The cut-outs are arranged to permit manually twisting of the hard cap. The second end of the hard cap has a pair of U-shaped cut-outs extending axially in the shell of the hard cap. The tabs of the rubber stopper as described in the above paragraph are arranged to insertively mate within the slot-like cut-outs on the second end of the hard cap. The hard cap has a pair of chamfered tabs extending ninety degrees away from the slot-like cut-outs. The chamfered tabs extend radially outwardly from the second end of the hard tab. The chamfered tabs are arranged so as to mating the engaged slots within the first end of the vial body. A flexible rubber cap-like diaphragm cover is matingly engagable with the hard cap. The rubber diaphragm end cap cover has an innermost post centrally disposed within an annular shell of a housing. The post is arranged so as to mate with the centrally disposed opening on the first end of the hard cap to sealingly engage therewith. Such a rubber diaphragm cover will keep the hard cap, the rubber stopper, and the first end of the vial body sterile.

In operation of the vial assembly, a biological specimen may be disposed within the inner chamber of the vial body. The hard cap is placed in a engaging relationship, so that the first end of the rubber stopper mates within the second end of the hard cap, the side tabs on the first end of the rubbers stopper mating with the slots on the second end of the hard cap. The second end of the rubber stopper is then pushed inwardly into the vial body, the elliptical shaped second end of the rubber stopper mates with the elliptical disposed walls just inwardly of the slots in the vial body. The side tabs on the second end of the hard cap are flexed slightly inwardly and snap outwardly once they engage the slots which are adjacent to the second end of the hard cap. Rotation of the hard cap, by manual engagement of the arcurate depressions of the first end thereof, permits the hard cap and the rubber stopper to be rotated about their joint longitudinal axes ninety degrees within the inner walls of the vial body. The elliptical shaped second end of the rubber stopper is compressed by virtue of its rotating with respect to the elliptical shaped walls within the vial body adjacent to the slots. This rotational action distorts the rubber stopper so as to compress the central bore therewithin. This compressed central bore with its conically shaped cut-out, thus seals the biological specimen within the main chamber of the vial body. Counter rotation of the hard cap and hence corresponding counter rotation of the rubber stopper, would effect an opening of the bore through the rubber stopper. The long axis of the elliptical bore within the rubber stopper is perpendicular to the long axis of the second end of the rubber stopper. By rotating the rubber stopper relative to the vial body, the central bore therethrough may thus be opened accordingly. The opening through the hard cap and hence the rubber stopper may be effected by rotation, so as to permit a sampling with a catheter of the Freedman type so as to permit a sampling or testing of the biological specimen within the main chamber of the vial assembly.

The second end of the vial body has a generally rectilinear or generally squared cross-sectional configuration. Thus, any biological sample would not be crushed by the inadvertent advancement of a catheter within that squared volume in the second chamber of the vial body, but would permit the mere sampling of such a specimen therewithin, without danger to the specimen itself.

The rubber diaphragm end cap cover is arranged to snap over the first end of the hard cap and provide a seal between the hard cap and the first end of the vial body, thus ensuring sterility therewithin.

Thus it has been shown a unique vial biological specimen container assembly which is readily adaptable for examination and for maintenance within a human uterine environment.

The invention thus includes a biological specimen container assembly for the safe storage and periodic examination of biological specimens therein, comprising an elongated vial having a primary chamber with a first open end and a second closed end, the second closed end on the vial having a secondary chamber therein of rectilinear or square cross-sectional shape than the first end, to permit its walls to be clear and readily viewed therethrough, for examination of its contents. A stopper has a first end and a second end, the second end being matable with the first open end of the vial, the stopper having an adjustably openable and closable bore extending longitudinally therethrough. A hard cap has a cavity therein which is matable over the first end of the stopper, and an end cap is matable over the hard cap and the stopper, the end cap being arranged to maintain sterility of the end cap, the stopper and first end of the vial. The primary chamber has an internal wall adjacent its open end, of elliptical cross-section, to permit deformation of the stopper when the stopper is rotated about its longitudinal axis therein. The stopper has a first end and a second end, said second end having an elliptical cross-sectional shape which is arranged to conformingly mate within the first end of the primary chamber. The hard cap has a first end with a central opening therethrough, the central opening arranged in longitudinal alignment with the bore in the stopper to permit a sampling catheter to be pressed therethrough. The hard cap and the stopper have mating interdigitating elements which permits the stopper to rotate about its longitudinal axis when the hard cap is rotated about its longitudinal axis. The second chamber is defined by a plurality of walls, at least one of the walls having a curvilinear thickness which functions as a magnifying glass to permit magnified visual examination of the contents of that second chamber. At Least one of said walls is also of uniform thickness thereacross, to permit examination of the contents of the second chamber by an external microscope. The container may have a filament attached thereto, to permit easy retrieval of the assembly from a biological situs.

The invention includes a method of maintaining a biological specimen in a safe condition, for development and medical examination of that specimen, comprising the steps of arranging the longitudinal axis of a generally cylindrically shaped vial having an open end with a first chamber thereat, and a closed end with a second chamber of generally square cross-section thereaccross, in a vertical orientation, depositing a biological specimen in the container, which specimen settles to the bottom of the squared second chamber, inserting a stopper or valve having a longitudinal bore therethrough, into mating engagement with the open end of the vial, placing a hard cap over the stopper to permit engagement therewith, and rotational twisting of the stopper within the open end of the vial; and covering the cap with a diaphragm cover to maintain the hard cap and the stopper sterile. The method includes the step of rotating the hard cap, and hence the stopper, to effect a deformation of the bore in the flexible stopper by engagement of the stopper with an inner section of wall of the first chamber, thus permitting entry to or closing access of the vial through the flexible stopper, without subjecting any biological sample in the vial to any changing of the volume or pressure within that vial. The method includes the step of forming the second chamber of a plurality of walls, at least one of which has a curvilinear thickness so as to form a lens to permit the magnified viewing of the contents of the second chamber of the vial.

The method includes the step of forming at least one of the walls comprising the second chamber, of uniform thickness, so as to permit non-distorted examination thereof by an external microscope. The method includes the step of shaping intermating portions of the stopper and the first chamber into corresponding elliptical configurations, so as to permit distortion of the stopper when the stopper is rotated about its longitudinal axis within the first chamber of the vial. The method includes the step of rotating the stopper about its longitudinal axis in the first chamber of the vial, to deform the stopper and the bore therethrough, to permit access to or seal a biological specimen within the vial without changing either pressure or volumetric effects on a specimen therein.

The invention also includes a biological specimen container assembly for the safe storage and subsequent examination of any biological specimen therein, comprising an elongated vial of generally cylindrical shape having a first open end and a second viewable closed end, a flexible stopper having a first end and a second end, the second end being sealably arranged in the open end of the vial, and a cap arranged on the first end of the flexible stopper to permit the stopper to be rotated with respect to the vial. The first open end of the vial has internal walls of elliptical configuration, the second end of the stopper having a corresponding elliptical configuration. The stopper has a bore therethrough, to permit access to any specimen in the vial The stopper may be rotated by twisting of the cap with respect to the vial to permit the bore in the stopper to be pinched to seal the specimen in the vial without effecting the pressure or volume of any specimen therein. The hard cap has an opening therein, which opening is in axial alignment with the bore in the stopper. The vial has at least one slot extending in a partial circumferential direction, and the hard cap has a corresponding radially extending tab arranged to engage that slot in the vial to permit the locking and tightening of the cap and stopper in the open end of the vial. A flexible end cover is arranged over the hard cap and the stopper to maintain sterility thereof. The second closed end comprises an internal chamber of generally square shape in cross section defined by the internal walls of the first end, so as to provide a protected volume for a biological specimen therein, unaffected by any probe injected within the first end of the vial. The second end has a wall portion having a curvilinear thickness therewith, which acts as a magnifying lens, to permit easy visual examination of any biological specimen within that second end of the vial.

BRIEF DESCRIPTION OF THE DRAWINGS

The objects and advantages of the present invention will become more apparent when viewed in conjunction with the following drawings, in which:

FIG. 2 is a side elevational view of a specimen container in its assembled configuration;

FIG. 3 is a sectional view taken along the sectional lines A—A of FIG. 2;

FIG. 4 is a side view of a vial of the present invention;

FIG. 5 is a sectional view taken along the sectional lines A—A of FIG. 4;

FIG. 6 is a sectional view taken along the sectional lines B—B of FIG. 4;

FIG. 7 is a sectional view taken along the sectional lines C—C of FIG. 4;

FIGS. 8a and 8b are perspective views of the first end of a rubber stopper constructed according to the principles of the present invention;

DESCRIPTION OF THE PREFERRED EMBODIMENTS

The present invention comprises a biological specimen container assembly 10, arranged to safely support a biological specimen in a controlled environment, such as in the uterus of a female.

Figure 1:
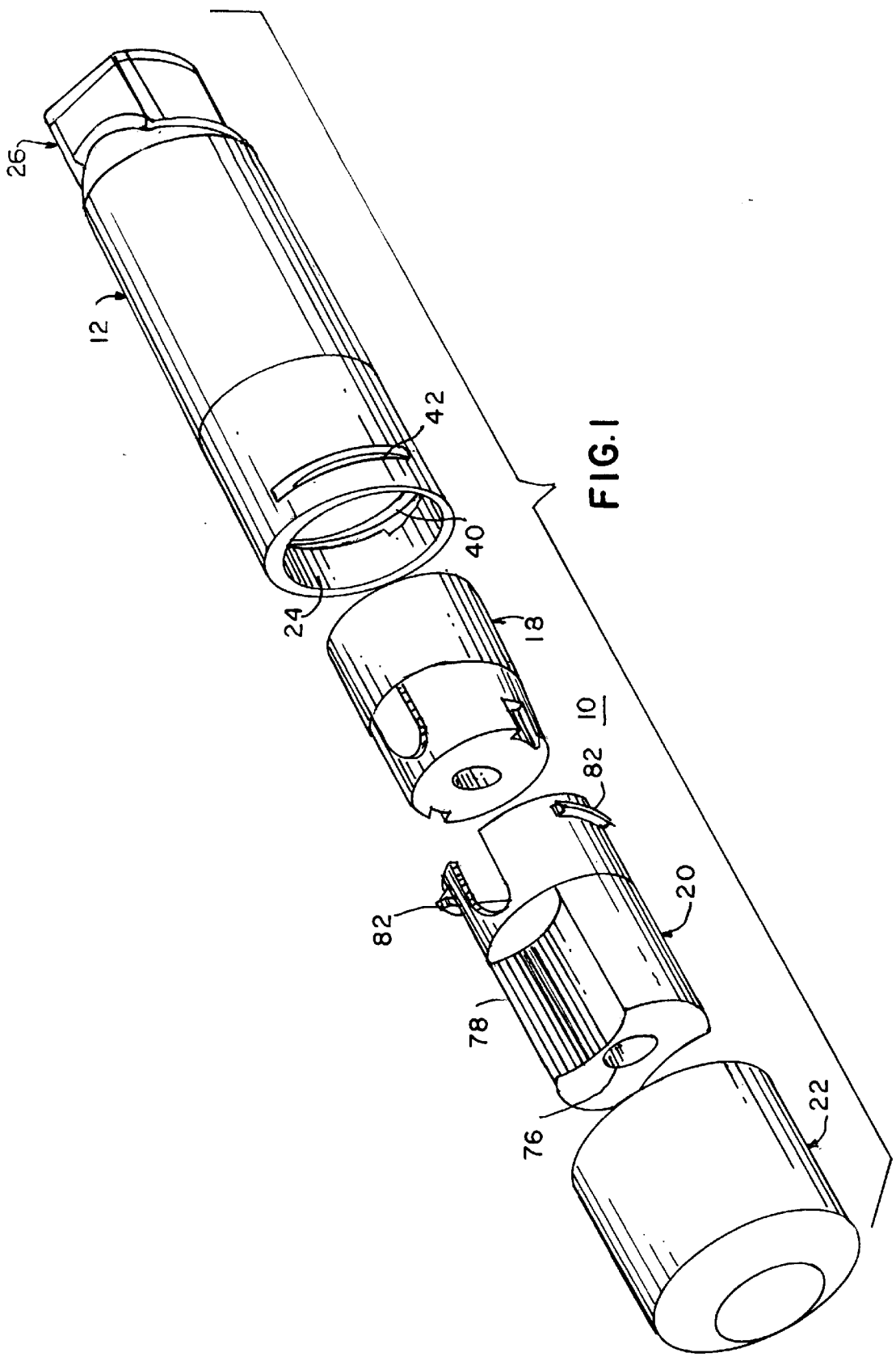
FIG. 1 is an exploded perspective view of a specimen container assembly, constructed according to the principles of the present invention.

The container assembly 10, as shown in FIG. 1, comprises a vial body portion 12 comprising a primary chamber 14 and a second chamber 16 of reduced internal and external dimensions compared to chamber 14, a rubber stopper or valve 18, a hard cap 20, and a rubber diaphragm cover 22. The vial body portion 12 is generally cylindrically shaped, having an opened first end 24 and a viewable closed second end 26, as shown in FIGS. 2, 3 and 4. The viewable closed second end 26 that comprises the second chamber 16, has a cross-section of generally square configuration, as shown in FIG. 7, which is a sectional view of FIG. 4. That is, the walls defining the viewable portion are of square configuration, having a pair of opposed first walls 30 and 32, and a pair of opposed second walls 34 and 36, one of the pair of first walls 30, being "lens shaped" and thicker, as shown in FIG. 7, so as to act as a focal area for visual viewing of a specimen contained within that viewable second chamber 16, at the closed end 26 of the vial body 12. One of the second walls 34 of the viewable portion of the vial body 12 at its closed end 26, has a wall section of constant uniform thickness, to permit microscopic examination of the contents of that chamber 16 within that closed end 26 of the vial body 12.

The vial body 12 has its main chamber 14 of generally cylindrical configuration. The first end 24 of the vial body 12 has a pair of opposed slots 40 and 42, as shown in FIGS. 2, 3 and 4, which are cut through the side wall of the vial body 12 adjacent the first opened end 24 thereof. Each slot 40 and 42 extends through an arc of about one hundred and twenty degrees. The chamber 14 has a wall portion 46 inwardly of the slots 40 and 42, which wall portion 46 defines an elliptical opening 50 adjacent the generally cylindrically shaped container chamber 14, as shown in FIG. 6. The vial body 12 may be made of a clear polycarbonate.

Figure 9:
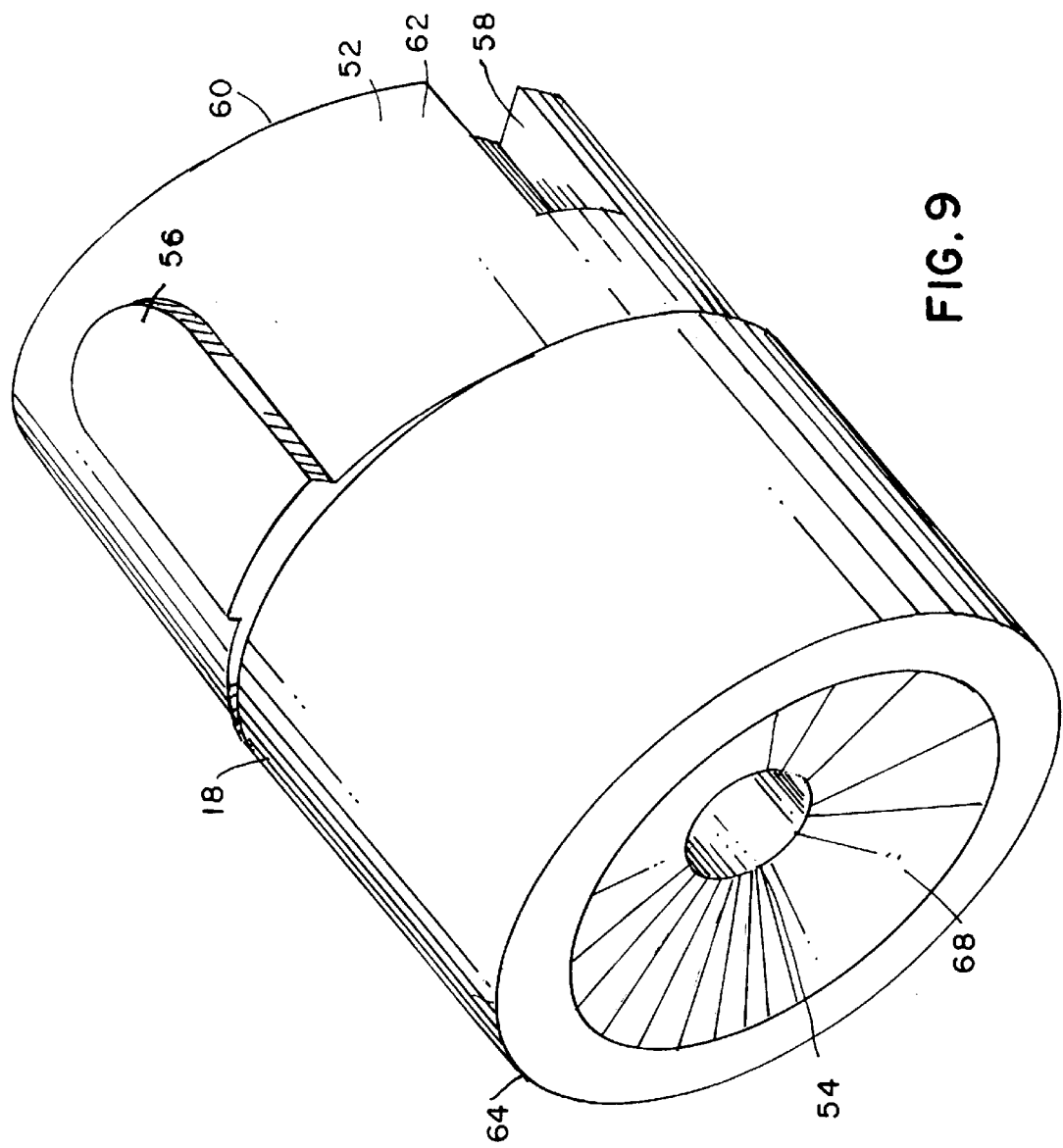
FIG. 9 is a perspective view of the second end of a rubber stopper constructed according to the principles of the present invention.
Figure 10A:
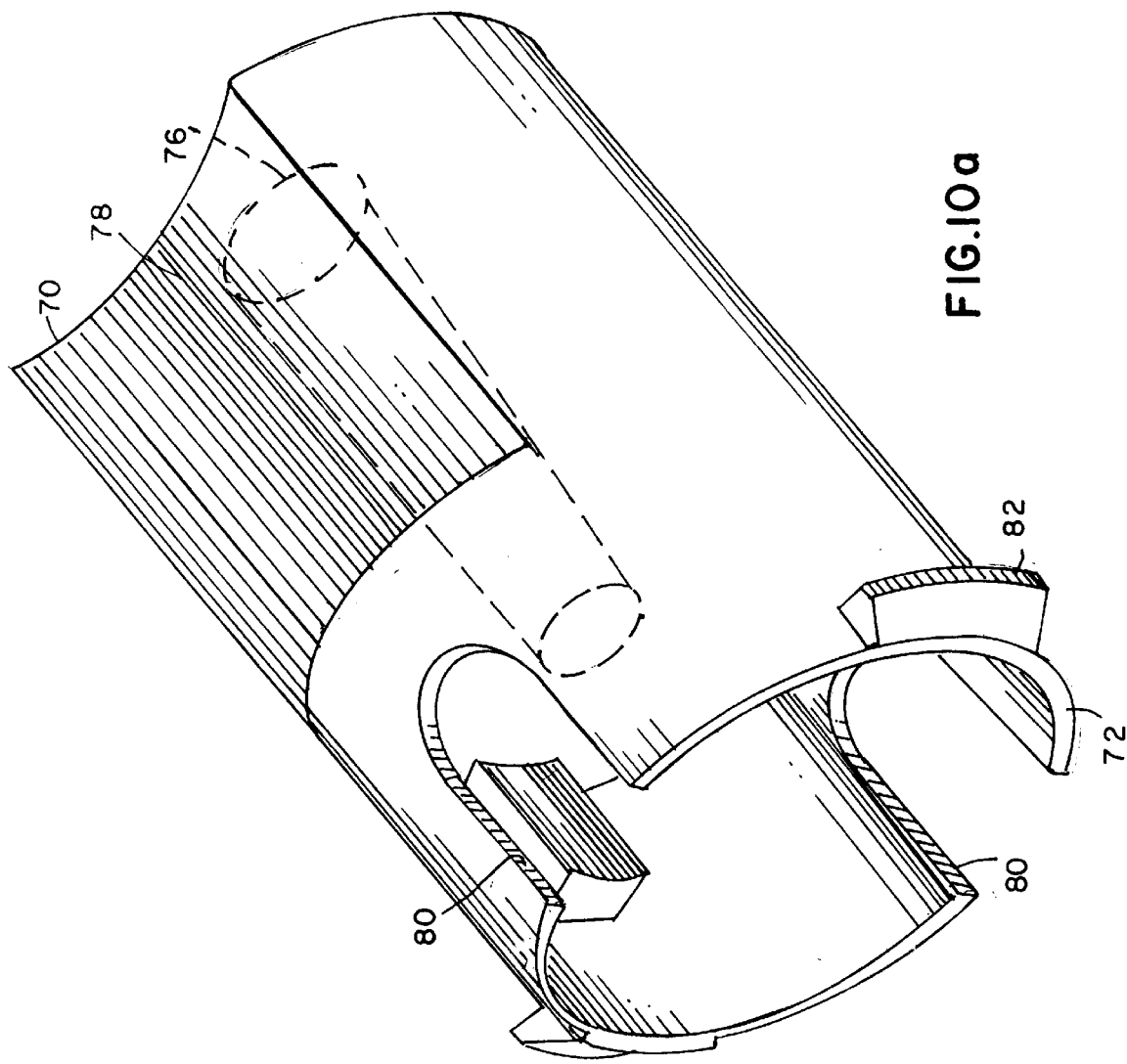
FIG. 10a is a perspective view oif the hard cap.
Figure 10B:
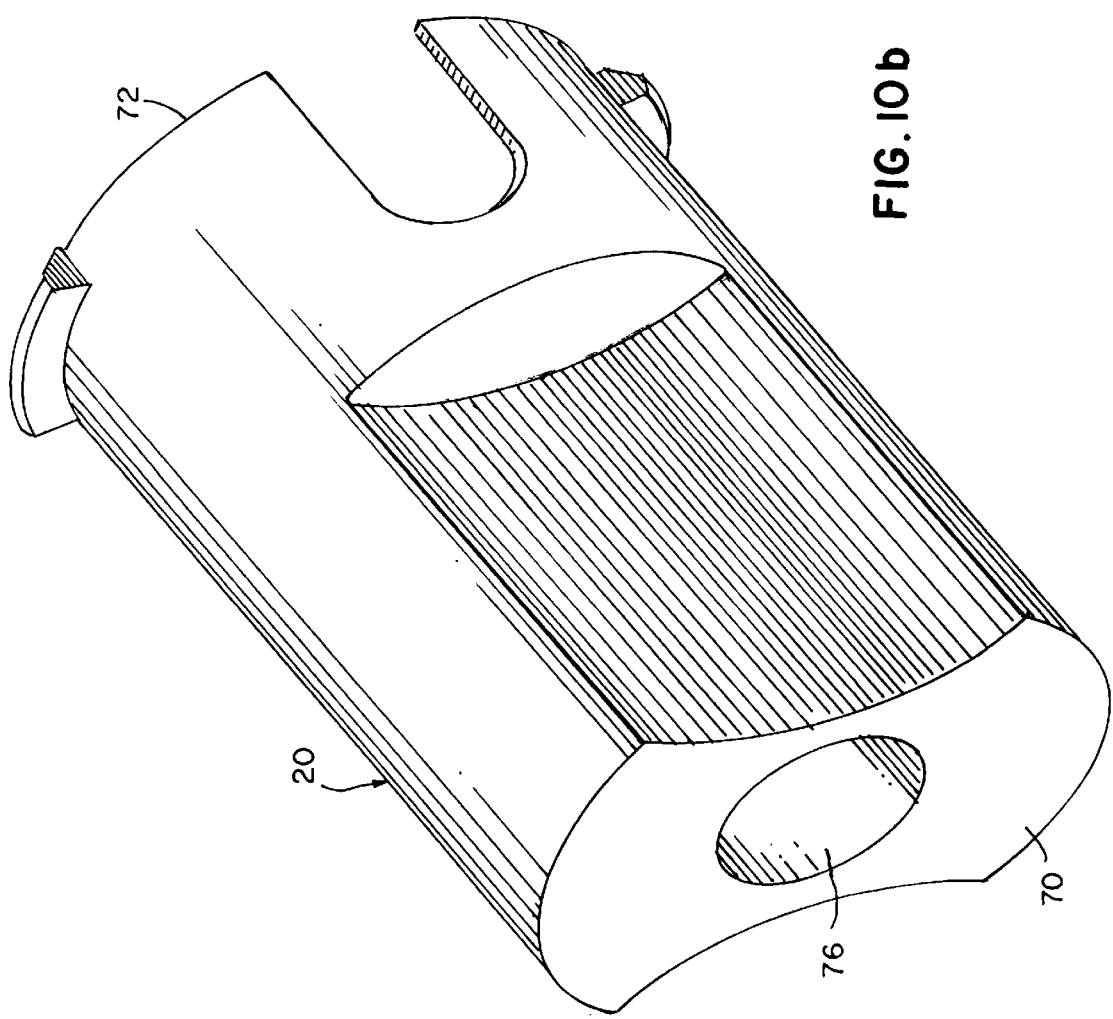
FIG. 10b is a perspective view of the second end of a hard cap constructed according to the principles of the present invention.

The assembly includes the rubber stopper or valve 18 which is cylindrically shaped on its first end 52, as shown in FIG. 8. The rubber stopper 18 has a longitudinal axis which is in alignment with the longitudinal axis of the vial body 12. The rubber stopper 18 has an elliptically shaped bore 54 extending longitudinally therethrough. The first end of the rubber stopper 18, comprising approximately one-half the longitudinally length of the rubber stopper 18, with a pair of opposed axially extending side tabs 56 thereon, adjacent the annular surface thereof. Spaced ninety degrees apart from the side tabs 56, are a pair of channel shaped cut-outs 58. The periphery 60 of the outer surface of the first end 52 of the rubber stopper 18, defines a circular surface 62, but for the side tabs 56. The rubber stopper 18 has a second end 64, contiguous to the first end 52, comprising the second longitudinal half thereof, and is of elliptical configuration, as shown in FIGS. 8 and 9. The second end 64 of the rubber stopper 18 has a conically shaped opening 68 which is in longitudinal alignment with the elliptical disposed bore 54 extending through the rubber stopper 18.

The vial assembly 10 includes a hard cap 20, as shown in FIG. 1. The hard cap 20 is a cup-shaped shell having a first end 70 and a second end 72. The first end 70 has a hole 76 extending therethrough, at a centermost location. The side walls of the first end 70 have a pair of opposed accurate shaped cut-outs 78 disposed thereacross. The cut-outs 78 are arranged to permit finger engagement for manually twisting of the hard cap 20. The second end 72 of the hard cap 20 has a pair of U-shaped cut-outs 80 extending axially in the shell of the hard cap 20. The tabs 56 of the rubber stopper 18 as described in the above paragraph, are arranged to mate within the slot-like cut-outs 80 on the second end 72 of the hard cap 20. The hard cap 20 has a pair of chamfered tabs 82 extending ninety degrees away from the slot-like cut-outs 80. The chamfered tabs 82 extend radially outwardly from the second end 72 of the hard cap 20. The chamfered tabs 82 are arranged so as to mating the engaged slots 40 and 42 within the first end 24 of the vial body 12. A flexible rubber cap-like diaphragm cover 22 is matingly engagable with the hard cap 20. The rubber diaphragm end cap cover 22 has an innermost post 86 centrally disposed therewithin. The post 86 is arranged so as to mate with the centrally disposed opening 76 on the first end of the hard cap 20, to sealingly engage therewith. Such a rubber diaphragm cover 22 will keep the hard cap 20, the rubber stopper 18, and the first end 24 of the vial body 12 sterile.

In operation of the vial assembly 10, a biological specimen may be disposed within the primary inner chamber 14 of the vial body 12. The hard cap 20 is placed in a engaging relationship, so that the first end of the rubber stopper 18 mates within the second end 72 of the hard cap 20, the side tabs 56 on the first end of the rubber stopper 18 mating with the slots 80 on the second end 72 of the hard cap 20. The second end of the rubber stopper 18 is then pushed inwardly into the vial body 12, the elliptical shaped second end 64 of the rubber stopper 18 mates with the elliptically shaped walls 46 just inwardly of the slots 40 and 42 in the vial body 12. The side tabs 82 on the second end 72 of the hard cap 20 are flexed slightly inwardly and snap outwardly once they engage the slots 40 and 42. Rotation of the hard cap 20, by manual engagement of the arcuate depressions 78 of the first end thereof permit the hard cap 20 and the rubber stopper 18 to be rotated ninety degrees, jointly about their common longitudinal axes, within the inner walls 46 of the vial body 12. The elliptically shaped second end 64 of the rubber stopper 18 is compressed by virtue of its rotating with respect to the elliptical shaped walls 46 within the vial body 12 adjacent to the slots 40 and 42. This rotational action distorts the rubber stopper 18 so as to compress the central bore 54 therewithin. This compressed central bore 54 with its conically shaped cut-out 68, thus seals the biological specimen within the main chamber 14 of the vial body 12. Counter rotation of the hard cap 20 and hence corresponding counter rotation of the rubber stopper 18, would effect an opening of the bore 54 through the rubber stopper 18. The long axis of the elliptical bore 54 within the rubber stopper 18 is perpendicular to the long axis of the elliptically shaped second end 64 of the rubber stopper 18. By rotating the rubber stopper 18 relative to the vial body 12, the central bore 54 therethrough may thus be opened accordingly. The opening 76 through the hard cap 20 and hence the rubber stopper 18 may be effected by rotation, so as to permit a sampling with a catheter of the Freedman type through those aligned opening 76 and 54, so as to permit a sampling or testing of the biological specimen within the main chamber 14 of the vial assembly 10.

The second end 26 of the vial body 12 has its squared cross-sectional dimensions, so as to permit the second chamber 16 therein, to be rectilinear, as opposed to the internal cylindrically shaped first end. Thus, any biological sample would not be crushed by the inadvertent advancement of such a catheter within that squared internally shaped second chamber 16 of the vial body, but would permit the mere sampling of such a specimen therewithin, without danger to the specimen itself.

The rubber diaphragm end cap cover 22 is arranged to snap over the first end 70 of the hard cap 20 and provide a seal between the hard cap 20 and the first end 24 of the vial body 12, thus ensuring sterility therewithin.

Thus it has been shown a unique vial biological specimen container assembly which is readily adaptable for examination and for maintenance within a human environment.

We claim:

1. A biological specimen container assembly for the safe storage and periodic examination of biological specimens therein, comprising:

an elongated vial having a primary chamber with a first open end and a viewable second closed end;

said second closed end on said vial having a secondary chamber therein of square cross-sectional shape;

a valve having a first end and a second end, said second end being matable with said first open end of said vial, said valve having an adjustably openable and squeezably closable bore during rotation of said valve with respect to said vial, said bore extending longitudinally through said valve;

a hard cap having a cavity therein which cap is matable over said first end of said valve;

an end cover matable over said hard cap and said valve, said end cover being arranged to maintain sterility of said cap, said valve and first end of said vial and said vial having at least one slot extending in a partial circumferential direction, and said hard cap has a corresponding radially extending tab arranged to engage said slot in said vial to permit the locking and tightening of said cap and valve in said open end of said vial.

2. The biological specimen container assembly as recited in claim 1, wherein said primary chamber has an internal wall adjacent its open end, of elliptical cross-section, wherein said valve has a first end and a second end, said second end having an elliptical cross-sectional shape which shape is arranged to conformingly mate within said first end of said primary chamber to permit deformation of said valve when said valve is rotated about its longitudinal axis therein.

3. The biological specimen container assembly as recited in claim 1, wherein said hard cap has a first end with a central opening therethrough, said central opening arranged in longitudinal alignment with said bore in said valve, to permit a catheter to be passed therethrough.

4. The biological specimen container assembly as recited in claim 3 wherein s aid hard cap and said valve have mating interdigitating elements which permits said valve to rotate about its longitudinal axis when said hard cap is rotated about its longitudinal axis.

5. The biological specimen container assembly as recited in claim 1, wherein said square shaped second chamber is defined by a plurality of walls, at least one of said walls having a curvilinear thickness which functions as a magnifying glass to permit magnified visual examination of the contents of said second chamber.

6. The biological specimen container assembly as recited in claim 5, wherein at least one of said walls is of uniform thickness thereacross, to permit examination of the contents of said second chamber by an external microscope.

7. The biological specimen container assembly as recited in claim 1, having a filament attached thereto, to permit easy retrieval of said assembly from a biological situs.

8. A method of maintaining a biological specimen in a safe condition, for development and medical examination of that specimen, comprising the steps of:

arranging the longitudinal axis of a generally cylindrically shaped vial having an open end with a first chamber thereat, and a closed end with a second chamber of generally rectilinear shape in cross section thereat, in a vertical orientation;

depositing a biological specimen in said vial, which specimen settles to said second rectilinear shaped chamber;

inserting a valve, into mating engagement with said open end of said vial, said valve having a squeezably closable bore therethrough upon rotative engagement of said valve with said open end of said vial;

placing a hard cap over said valve to permit rotational twisting of said valve within said open end of said vial; and covering said cap with a diaphragm cover to maintain said hard cap and said valve sterile, forming at least one slot extending in a partial circumferential direction in said vial, said hard cap having a corresponding radially extending tab arranged to engage said slot in said vial to permit the locking and tightening of said cap and valve in said open end of said vial.

9. The method of claim 8, including the step of:

rotating said hard, cap, and hence said valve, to effect a deformation of said bore in said valve by engagement of said valve with a section of wall of said first chamber, thus permitting entry to or closing access of said vial through said valve, without subjecting any biological sample in said vial to any changing of the volume or pressure within said vial.

10. The method of claim 9, including the step of:

forming said chamber of a plurality of walls, at least one of which has a curvilinear thickness so as to form a lens to permit the magnified viewing of the contents of the second chamber of said vial.

11. The method of claim 10, including the step of:

forming at least one of said walls comprising said second chamber, of uniform thickness, so as to permit non-distorted examination thereof by an external microscope.

12. The method of claim 8, including the step of:

shaping intermating portions of said valve and said first chamber into corresponding elliptical configurations, so as to permit distortion of said valve and hence distortion of said bore therethrough when said valve is rotated about its longitudinal axis within said first chamber of said vial to close said bore when said elliptical configurations of said valve and said first chamber are out of correspondence.

13. The method of claim 12, including the step of:

rotating said valve about its longitudinal axis in said first chamber of said vial, to deform said valve and said bore therethrough, to permit access to or seal a biological specimen within said vial without changing either pressure or volume with respect to said specimen.

14. A biological specimen container assembly for the safe storage and subsequent examination of any biological specimen therein, comprising:

an elongated vial of generally cylindrical shape having a first open end and a second closed end;

a flexible valve having a first end and a second end, said second end being sealably arranged in said open end of said vial; and a hard cap with an opening therethrough arranged on said first end of said flexible valve to permit said valve to be rotated with respect to said vial;

said first open end of said vial having internal walls of elliptical configuration, said second end of said valve having a corresponding elliptical configuration, said valve having a bore therethrough, to permit access to any specimen in said vial therethrough;

said valve being rotatable by twisting of said hard cap with respect to said vial to permit said bore in said valve to be pinched to seal said specimen in said vial without effecting the pressure or volume of said specimen therein; and said vial has at least one slot extending in a partial circumferential direction, and said hard cap has a corresponding radially extending tab arranged to engage said slot in said vial to permit the locking and tightening of said cap and valve in said open end of said vial.

15. The biological specimen container assembly as recited in claim 14, wherein said opening in said hard cap in axial alignment with said bore in said valve.

16. The biological specimen container assembly as recited in claim 14, wherein a flexible end cover is arranged over said hard cap and said valve to maintain sterility thereof.

17. The biological specimen container assembly as recited in claim 14, wherein said second closed end comprised an internal chamber of generally rectilinear shape in cross-section than said first end, so as to permit a viewable section at said second end of said vial.

18. The biological specimen container assembly as recited in claim 14, wherein said second end has a wall portion having a curvilinear thickness therewith, which acts as a magnifying lens, to permit visual examination of any biological specimen within said second end of said vial.

* * * * *